United States Patent
Chao et al.

(12) 
(10) Patent No.: US 6,759,439 B2
(45) Date of Patent: *Jul. 6, 2004

(54) FISCHER-TROPSCH PROCESSES AND CATALYSTS WITH PROMOTERS

(75) Inventors: Wenchun Chao, State College, PA (US); Kamel M. Makar, Wilmington, DE (US); Leo E. Manzer, Wilmington, DE (US); Munirpallam A. Subramanian, Kennett Square, PA (US)

(73) Assignee: ConocoPhillips Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/308,494

(22) Filed: Dec. 3, 2002

(65) Prior Publication Data

US 2003/0119922 A1 Jun. 26, 2003

Related U.S. Application Data

(63) Continuation of application No. 09/939,312, filed on Aug. 24, 2001, now Pat. No. 6,489,371, which is a division of application No. 09/314,811, filed on May 19, 1999, now Pat. No. 6,333,294, and a continuation of application No. 09/804,271, filed on Mar. 12, 2001, now abandoned.

(60) Provisional application No. 60/097,180, filed on Aug. 20, 1998, provisional application No. 60/086,372, filed on May 22, 1998, and provisional application No. 60/086,405, filed on May 22, 1998.

(51) Int. Cl.$^7$ .............................................. C07C 27/00
(52) U.S. Cl. ...................... 518/715; 518/717; 518/721
(58) Field of Search ............................. 518/700, 715, 518/717, 721

(56) References Cited

U.S. PATENT DOCUMENTS 5,028,634 A * 7/1991 Fiato ........................... 518/707

OTHER PUBLICATIONS

M.J. Philips et al, Proceedings 9th International Congress on Catalysis, vol. 2, 1988.*

* cited by examiner

Primary Examiner—J. Parsa
(74) Attorney, Agent, or Firm—Conley Rose

(57) ABSTRACT

A process is disclosed for producing hydrocarbons. The process involves contacting a feed stream comprising hydrogen and carbon monoxide with a catalyst in a reaction zone maintained at conversion-promoting conditions effective to produce an effluent stream comprising hydrocarbons. In accordance with this invention, the catalyst used in the process preferably includes at least cobalt, rhenium, and a promoter selected from the group including boron, phosphorus, potassium, manganese, and vanadium. The catalyst may also comprise a support material selected from the group including silica, titania, titania/alumina, zirconia, alumina, aluminum fluoride, and fluorided aluminas.

9 Claims, No Drawings

FISCHER-TROPSCH PROCESSES AND CATALYSTS WITH PROMOTERS

CROSS-REFERENCE TO RELATED APPLICATIONS

The present application is a continuation of U.S. application Ser. No. 09/939,312 filed Aug. 24, 2001 now U.S. Pat. No. 6,489,371, which is a divisional application of U.S. utility application Serial No. 09/314,811 filed May 19, 1999, now U.S. Pat. No. 6,333,294. The present application is also a continuation of U.S. application Ser. No. 09/804,271 filed Mar. 12, 2001, now abandoned which is a continuation-in-part of U.S. Ser. No. 09/314,811 filed May 19, 1999, now U.S. Pat. No. 6,333,294. U.S. application Ser. No. 09/314,811 claims the benefit of U.S. provisional patent application Serial No. 60/086,372, filed May 22, 1998, U.S. provisional patent application Serial No. 60/086,405, filed May 22, 1998, and of U.S. provisional patent application Serial No. 60/097,180, filed Aug. 20, 1998. All of the above-mentioned applications are incorporated herein by reference in their entirety.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, (i.e., a mixture of carbon monoxide and hydrogen), typically labeled the Fischer-Tropsch process. Particularly, this invention relates to the use of aluminum fluoride or fluorided alumina supported catalysts containing cobalt and rhenium and at least one other element selected from boron, phosphorus, potassium, manganese and vanadium, for the Fischer-Tropsch process.

BACKGROUND OF THE INVENTION

Large quantities of methane, the main component of natural gas, are available in many areas of the world. Methane can be used as a starting material for the production of hydrocarbons. The conversion of methane to hydrocarbons is typically carried out in two steps. In the first step methane is reformed with water or partially oxidized with oxygen to produce carbon monoxide and hydrogen (i.e., synthesis gas or syngas). In a second step, the syngas is converted to hydrocarbons.

This second step, the preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active metal of Groups 8, 9, 10 (in the New notation of the periodic table of the elements, which is followed throughout). In particular, iron, cobalt, nickel, and ruthenium have been abundantly used as the catalytically active metals. Cobalt and ruthenium have been found to be most suitable for catalyzing a process in which synthesis gas is converted to primarily hydrocarbons having five or more carbon atoms (i.e., where the $C_5^+$ selectivity of the catalyst is high). Additionally, the catalysts often contain one or more promoters and a support or carrier material. Rhenium is a widely used promoter.

The Fischer-Tropsch reaction involves the catalytic hydrogenation of carbon monoxide to produce a variety of products ranging from methane to higher aliphatic alcohols. The methanation reaction was first described in the early 1900's, and the later work by Fischer and Tropsch dealing with higher hydrocarbon synthesis was described in the 1920's.

The Fischer-Tropsch synthesis reactions are highly exothermic and reaction vessels must be designed for adequate heat exchange capacity. Because the feed streams to Fischer-Tropsch reaction vessels are gases while the product streams include liquids, the reaction vessels must have the ability to continuously produce and remove the desired range of liquid hydrocarbon products. The process has been considered for the conversion of carbonaceous feedstock, e.g., coal or natural gas, to higher value liquid fuel or petrochemicals. The first major commercial use of the Fischer-Tropsch process was in Germany during the 1930's. More than 10,000 B/D (barrels per day) of products were manufactured with a cobalt based catalyst in a fixed-bed reactor. This work has been described by Fischer and Pichler in Ger. Pat. No. 731,295 issued Aug. 2, 1936.

Motivated by production of high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Tex., using powdered iron as the catalyst. Due to disappointing levels of conversion, scale-up problems, and rising natural gas prices, operations at this plant were suspended in 1957. Research has continued, however, on developing Fischer-Tropsch reactors such as slurry-bubble columns, as disclosed in U.S. Pat. No. 5,348,982 issued Sep. 20, 1994.

Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research is likewise continuing on the development of more efficient Fischer-Tropsch catalyst systems and reaction systems that increase the selectivity for high-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution or product selectivity depends heavily on the type and structure of the catalysts and on the reactor type and operating conditions. Accordingly, it is highly desirable to maximize the selectivity of the Fischer-Tropsch synthesis to the production of high-value liquid hydrocarbons, such as hydrocarbons with five or more carbon atoms per hydrocarbon chain.

U.S. Pat. No. 4,659,681 issued on Apr. 21, 1987, describes the laser synthesis of iron based catalyst particles in the 1–100 micron particle size range for use in a slurry reactor for Fischer-Tropsch synthesis.

U.S. Pat. No. 4,619,910 issued on Oct. 28, 1986, and U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure.

The catalysts are activated in a fixed-bed reactor by reaction with CO+H$_2$ prior to slurrying in the oil phase in the absence of air.

Catalyst supports for catalysts used in Fischer-Tropsch synthesis of hydrocarbons have typically been oxides (e.g., silica, alumina, titania, zirconia or mixtures thereof, such as silica-alumina). It has been claimed that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). The products prepared by using these catalysts usually have a very wide range of molecular weights.

U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst. U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group 3 or Group 4 metal oxide, e.g., thoria. European Patent No. 142,887 discloses a silica supported cobalt catalyst together with zirconium, titanium, ruthenium and/or chromium.

International Publication Nos. WO 98/47618 and WO 98/47620 disclose the use of rhenium promoters and describe several functions served by the rhenium.

U.S. Pat. No. 5,248,701 discloses a copper promoted cobalt-manganese spinel that is said to be useful as a Fischer-Tropsch catalyst with selectivity for olefins and higher paraffins.

Despite the vast amount of research effort in this field, promoted Fischer-Tropsch catalysts using aluminum fluoride or fluorided alumina supports are not known in the art. There is still a great need to identify new catalysts for Fischer-Tropsch synthesis, particularly catalysts that provide high $C_5^+$ hydrocarbon selectivities to maximize the value of the hydrocarbons produced and thus the process economics.

SUMMARY OF THE INVENTION

This invention provides a process for producing hydrocarbons, and a method for preparing the catalyst. The process comprises contacting a feed stream comprising hydrogen and carbon monoxide with a catalyst in a reaction zone maintained at conversion-promoting conditions effective to produce an effluent stream comprising hydrocarbons.

This invention also provides a process for producing hydrocarbons, comprising contacting a feed stream comprising hydrogen and carbon monoxide with a supported catalyst in a reaction zone maintained at conversion-promoting conditions effective to produce an effluent stream comprising hydrocarbons. In accordance with this invention, the catalyst used in the process comprises cobalt, optionally rhenium, and at least one element selected from the group consisting of boron, phosphorus, potassium, manganese, and vanadium, and one or more support materials selected from the group including silica, titania, titania/alumina, zirconia, alumina, aluminum fluoride, and fluorided aluminas.

DETAILED DESCRIPTION OF THE INVENTION

The feed gases charged to the process of the invention comprise hydrogen, or a hydrogen source, and carbon monoxide. H$_2$/CO mixtures suitable as a feedstock for conversion to hydrocarbons according to the process of this invention can be obtained from light hydrocarbons such as methane by means of steam reforming, partial oxidation, or other processes known in the art. Preferably the hydrogen is provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). Preferably, the feed gas stream contains hydrogen and carbon monoxide in a molar ratio of about 2:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column, reactive distillation column, or ebullating bed reactors, among others, may be used. Accordingly, the size and physical form of the catalyst particles may vary depending on the reactor in which they are to be used.

The active catalyst components used in this invention are carried or supported on a support selected from the group including silica, titania, titania/alumina, zirconia, alumina, aluminum fluoride, and fluorided alumina, silica, titania, and titania/alumina. Aluminum fluoride supports are defined as at least one aluminum fluoride (e.g., alpha-AlF$_3$, beta-AlF$_3$, delta-AlF$_3$, eta-AlF$_3$, gamma-AlF$_3$, kappa-AlF$_3$ and/or theta-AlF$_3$). Preferred supports include alumina and aluminum fluoride. Preferred aluminum fluoride supports are aluminum fluorides that are primarily alpha-AlF$_3$ and/or beta-AF$_3$.

Fluorided alumina is defined as a composition comprising aluminum, oxygen, and fluorine. The fluoride content of the fluorided alumina can vary over a wide range, from about 0.001% to about 67.8% by weight. Preferred are fluorided aluminas containing from 0.001% to about 10% by weight fluorine. The remainder of the fluorided alumina component will include aluminum and oxygen. The composition may also contain a minor amount (compared to aluminum) of silicon, titanium, phosphorus, zirconium and/or magnesium.

The support material comprising fluorided aluminas and/or an aluminum fluoride may be prepared by a variety of methods. For example, U.S. Pat. Nos. 4,275,046 and 4,902,838 and 5,243,106 disclose the preparation of fluorided alumina by the reaction of alumina with a vaporizable fluorine-containing fluorinating compound. Suitable fluorinating compounds include HF, CCl$_3$F, CCl$_2$F$_2$, CHClF$_2$, CH$_3$CHF$_2$, CCl$_2$FCClF$_2$ and CHF$_3$. U.S. Pat. No. 5,243,106 discloses the preparation of a high purity AlF$_3$ from aluminum sec-butoxide and HF.

Metals can be supported on aluminum fluoride or on fluorided alumina in a variety of ways. For example, U.S. Pat. No. 4,766,260 discloses the preparation of metals such as cobalt on a fluorided alumina support using impregnation techniques to support the metal. U.S. Pat. No. 5,559,069 discloses the preparation of a multiphase catalyst composition comprising various metal fluorides including cobalt fluoride homogeneously dispersed with aluminum fluoride. PCT Int. Publ. No. 97/19751 discloses the preparation of multiphase catalyst compositions comprising metallic ruthenium homogeneously dispersed with various metal fluorides including aluminum fluoride.

Phases of aluminum fluoride such as eta, beta, theta and kappa can be prepared as described in U.S. Pat. Nos. 5,393,509, 5,417,954, and 5,460,795.

Aluminas that have been treated with fluosilicic acid ($H_2SiF_6$) such as those described in European Patent Application No. EP 497,436 can also be used as a support. The disclosed support comprises from about 0.5 to about 10 weight percent of fluorine, from 0.5 to about 5 weight percent of silica and from about 85 to about 99 weight percent of alumina.

The catalyst contains a catalytically effective amount of cobalt and rhenium. The amount of cobalt and rhenium present in the catalyst may vary widely. Typically, the catalyst comprises from about 1 to 50% by weight (as the metal) of the total supported cobalt and rhenium per total weight of catalytic metal and support, preferably from about 1 to 30% by weight, and more preferably from about 1 to 25% by weight. Rhenium is added to the support in a concentration sufficient to provide a weight ratio of elemental rhenium:elemental cobalt of from about 0.001:1 to about 0.25:1, preferably from about 0.001:1 to about 0.05:1 (dry basis).

We have found that higher selectivity and productivity catalysts are produced when a promoter selected from the group consisting of boron, phosphorus, potassium, manganese and vanadium is added to the cobalt-rhenium catalyst. This is quite surprising because boron and phosphorus are typically considered to be Fischer-Tropsch catalyst poisons. Additionally, and even more surprisingly, the catalysts of the present invention exhibit both improved conversion and improved stability, with long lifetime, relative to prior art Fischer-Tropsch catalysts. The conversion is particularly high in the case of the boron and manganese promoted catalysts of the present invention, and can equal or approach 100%. The amount of promoter is added to the cobalt-rhenium catalyst in a concentration sufficient to provide a weight ratio of elemental promoter: elemental cobalt of from about 0.00005:1 to about 0.5:1, preferably, from about 0.0005:1 to about 0.01:1. (dry basis).

The catalysts of the present invention may be prepared by any of the methods known to those skilled in the art. By way of illustration and not limitation, such methods include impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention maybe used in the form of powders, particles, pellets, monoliths, honeycombs, packed beds, foams, and aerogels.

The most preferred method of preparation may vary among those skilled in the art, depending for example on the desired catalyst particle size. Those skilled in the art are able to select the most suitable method for a given set of requirements.

One method of preparing a supported metal catalyst (e.g., a supported cobalt, cobalt/rhenium, or cobalt/rhenium/promoter catalyst) is by incipient wetness impregnation of the support with an aqueous solution of a soluble metal salt such as nitrate, acetate, acetylacetonate or the like. Another method of preparing a supported metal catalyst is by a melt impregnation technique, which involves preparing the supported metal catalyst from a molten metal salt. One preferred method is to impregnate the support with a molten metal nitrate (e.g., $Co(NO_3)_2 \cdot 6H_2O$). Alternatively, the support can be impregnated with a solution of zero valent metal precursor. One preferred method is to impregnate the support with a solution of zero valent cobalt such as $Co_2(CO)_8$, $Co_4(CO)_{12}$ or the like in a suitable organic solvent (e.g., toluene). Suitable rhenium compounds are the common water soluble ones, e.g., rhenium heptoxide ($Re_2O_7$) and ammonium perrhenate ($NH_4ReO_4$).

The impregnated support is dried and reduced with hydrogen or a hydrogen containing gas. The hydrogen reduction step may not be necessary if the catalyst is prepared with zero valent cobalt. In another preferred method, the impregnated support is dried, oxidized with air or oxygen and reduced in the presence of hydrogen.

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as may a mixture of hydrogen and an inert gas such as nitrogen, or a mixture of hydrogen and other gases as are known in the art, such as carbon monoxide and carbon dioxide. Reduction with pure hydrogen and reduction with a mixture of hydrogen and carbon monoxide are preferred. The amount of hydrogen may range from about 1% to about 100% by volume.

The Fischer-Tropsch process is typically run in a continuous mode. In this mode, the gas hourly space velocity through the reaction zone typically may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), and still more preferably, from about 140 psig (1066 kPa) to about 400 psig (2858 kPa).

The products resulting from the process will have a great range of molecular weights. Typically, the carbon number range of the product hydrocarbons will start at methane and continue to the limits observable by modern analysis, about 50 to 100 carbons per molecule. The process is particularly useful for making hydrocarbons having five or more carbon atoms especially when the above-referenced preferred space velocity, temperature and pressure ranges are employed.

The wide range of hydrocarbons produced in the reaction zone will typically afford liquid phase products at the reaction zone operating conditions. Therefore the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art scan, using the description herein, utilize the present invention to its fullest extent. The following embodiments are to be construed as illustrative, and not as constraining the scope of the present invention in any way whatsoever.

EXAMPLES

General Procedure For Batch Tests

Each of the catalyst samples was treated with hydrogen prior to use in the Fischer-Tropsch reaction. The catalyst sample was placed in a small quartz crucible in a chamber and purged with 500 sccm ($8.3 \times 10^{-6}$ m$^3$/s) nitrogen at room temperature for 15 minutes. The sample was then heated under 100 sccm ($1.7 \times 10^{-6}$ m$^3$/s) hydrogen at 1° C./minute to 100° C. and held at 100° C. for one hour. The catalysts were then heated at 1° C./minute to 400° C. and held at 400° C. for four hours under 100 sccm ($1.7 \times 10^{-6}$ m$^3$/s) hydrogen. The samples were cooled in hydrogen and purged with nitrogen before use.

A 2 mL pressure vessel was heated at either 200° C. or 225° C. under 1000 psig (6994 kPa) of $H_2$:CO (2:1) and maintained at that temperature and pressure for 1 hour. In a typical run, roughly 50 mg of the reduced catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of $C_{11}$–$C_{40}$ were analyzed relative to the internal standard. The lower hydrocarbons were not analyzed since they are masked by the solvent and are also vented as the pressure is reduced.

A $C_{11}^+$ Productivity (g $C_{11}^+$/hour/kg catalyst) was calculated based on the integrated production of the $C_{11}$–$C_{40}$ hydrocarbons per kg of catalyst per hour. The logarithm of the weight fraction for each carbon number $1(W_n/n)$ was plotted as the ordinate vs. number of carbon atoms in $(W_n/n)$ as the abscissa. From the slope, a value of alpha was obtained. Some runs displayed a double alpha as shown in the tables. The results of runs over a variety of catalysts at 200° C. are shown in Table 1.

Catalyst Preparation

EXAMPLE 1

$Re_2O_7$ (0.0650 g) and $B_2O_3$ (0.0016 g) were dissolved in a small amount of water, added to molten $Co(NO_3)_2 \cdot 6H_2O$ (4.9384 g) and mixed well. Engelhard fluorided alumina (4352–3.95 g) was slurried into this solution. The slurry was dried at 80° C. The solids were removed from the oven and exposed to air to absorb moisture. The solids were then dried again at 80° C. followed by heating the solids at 0.5° C. per minute to 350° C. and maintaining the solids at this temperature for 18 minutes. The solids were then reduced in hydrogen flow at 450° C. for 6 hours. The material was cooled and flushed with nitrogen overnight and then sealed for transport into an inert atmosphere glove box. The recovered catalyst was bottled and sealed for storage inside the glove box until Fischer-Tropsch testing could be completed. The catalyst had a nominal composition of 20%Co/1.0%Re/0.01%B/Al$_2$O$_3$(F). This catalyst was also used in Example 17.

EXAMPLE 2

The same procedure and materials as used in example 1 were used, except that 0.0080 g of $B_2O_3$ was used. The catalyst had a nominal composition of 20%Co/1.0%Re/0.05%B/Al$_2$O$_3$(F). This catalyst was also used in Example 18.

EXAMPLE 3

The same procedure and materials as used in example 1 were used, except that 0.0161 g of $B_2O_3$ was used. The catalyst had a nominal composition of 20%Co/1.0%Re/0.1%B/Al$_2$O$_3$(F). This catalyst was also used in Example 19.

EXAMPLE 4

The same procedure and materials as used in example 1 were used, except that Al$_2$O$_3$ (Chimet, 3.9500 g) and $P_2O_5$ (0.0011 g) was used. The catalyst had a nominal composition of 20%Co/1.0%Re/0.01%P/Al$_2$O$_3$. This catalyst was also used in Example 20.

EXAMPLE 5

The same procedure and materials as used in example 4 were used, except that 0.0055 g of $P_2O_5$ was used. The catalyst had a nominal composition of 20%Co/1.0%Re/0.05%P/Al$_2$O$_3$. This catalyst was also used in Example 21.

EXAMPLE 6

The same procedure and materials as used in example 4 were used, except that 0.0110 g of $P_2O_5$ was used. The catalyst had a nominal composition of 20%Co/1.0%Re/0.1%P/Al$_2$O$_3$. This catalyst was also used in Example 22.

EXAMPLE 7

The same procedure and materials as used in example 4 were used, except that 3.9250 g of Al$_2$O$_3$ and 0.0550 g of $P_2O_5$ were used. The catalyst had a nominal composition of 20%Co/1.0%Re/0.5%P/Al$_2$O$_3$. This catalyst was also used in Example 23.

EXAMPLE 8

The same procedure and materials as used in example 7 were used, except that 3.9000 g of Al$_2$O$_3$ and 0.1100 g of $P_2O_5$ were used. The catalyst had a nominal composition of 20%Co/1.0%Re/1.0%P/Al$_2$O$_3$. This catalyst was also used in Example 24.

EXAMPLE 9

The same procedure and materials as used in example 1 were used, except that Al$_2$O$_3$ (Chimet, 3.9500 g) and $B_2O_3$ (0.0161 g) were used. The catalyst had a nominal composition of 20%Co/1.0%Re/0.1%B/Al$_2$O$_3$. This catalyst was also used in Example 25.

EXAMPLE 10

The same procedure and materials as used in example 1 were used, except that $Al_2O_3$ (Chimet, 3.9250 g) and $B_2O_3$ (0.0805 g) were used. The catalyst had a nominal composition of 20%Co/1.0%Re/0.5%B/$Al_2O_3$. This catalyst was also used in Example 26.

EXAMPLE 11

The same procedure and materials as used in example 1 were used, except that $Al_2O_3$ (Chimet, 3.925 g) $NH_4ReO_4$ (0.1080 g) and $KNO_3$ (0.0065 g) were used. The catalyst had a nominal composition of 20%Co/1.5%Re/0.05%K/$Al_2O_3$.

EXAMPLE 12

The same procedure and materials as used in example 1 were used, except that $Al_2O_3$ (Chimet, 3.8975 g), $NH_4ReO_4$ (0.1440 g) and $Mn(NO_3)_2$ (0.0160 g) were used. The catalyst had a nominal composition of 20%Co/2.0%Re/0.1%Mn/$Al_2O_3$. This catalyst was also used in EXAMPLE 27

EXAMPLE 13

The same procedure and materials as used in example 1 were used, except that. $Al_2O_3$ (Chimet, 3.8925 g), $NH_4ReO_4$ (0.1440 g) and $Mn(NO_3)_2$ (0.0480 g) were used. The catalyst had a nominal composition of 20%Co/2.0%Re/0.3%Mn/$Al_2O_3$. This catalyst was also used in Example 28.

EXAMPLE 14

The same procedure and materials as used in example 1 were used, except that $Al_2O_3$ (Chimet 3.8750 g), $NH_4ReO_4$ (0.1440 g) and $Mn(NO_3)_2$ (0.1610 g) were used. The catalyst had a nominal composition of 20%Co/2.0%Re/1.0%Mn/$Al_2O_3$. This catalyst was also used in Example 29.

EXAMPLE 15 the same procedure and materials as used in example 1 were used, except that $Al_2O_3$ (Chimet 3.975 g), $Re_2O_7$ (0.0650 g) and $NH_4VO_3$ (0.0287 g) were used. The catalyst had a nominal composition of 20%Co/1.0%Re/0.25%V/$Al_2O_3$.

EXAMPLE 16 the same procedure and materials as used in example 1 were used, except that $A_2O_3$ (Chimet 3.925 g), $Re_2O_7$ (0.0650 g) and $NH_4VO_3$ (0.0574 g) were used. The catalyst had a nominal composition of 20%Co/1.0%Re/0.5%V/$Al_2O_3$.

TABLE 1

| Ex. No. | Catalyst | $C_{11}$+ Productivity | Alpha |
|---|---|---|---|
| 1 | 20% Co/1.0% Re/0.01% B/$Al_2O_3$(F) | 753 | 0.89 |
| 2 | 20% Co/1.0% Re/0.05% B/$Al_2O_3$(F) | 747 | 0.88 |
| 3 | 20% Co/1.0% Re/0.1% B/$Al_2O_3$(F) | 714 | 0.88 |
| 4 | 20% Co/1.0% Re/0.01% P/$Al_2O_3$ | 866 | 0.9 |
| 5 | 20% Co/1.0% Re/0.05% P/$Al_2O_3$ | 716 | 0.87 |
| 6 | 20% Co/1.0% Re/0.1% P/$Al_2O_3$ | 779 | 0.89 |
| 7 | 20% Co/1.0% Re/0.5% P/$Al_2O_3$ | 716 | 0.9 |
| 8 | 20% Co/1.0% Re/1% P/$Al_2O_3$ | 676 | 0.89 |
| 9 | 20% Co/1.0% Re/0.1% B/$Al_2O_3$ | 819 | 0.89 |
| 10 | 20% Co/1.0% Re/0.5% B/$Al_2O_3$ | 957 | 0.89 |
| 11 | 20% Co/1.0% Re/0.05% K/$Al_2O_3$ | 741 | 0.89 |
| 12 | 20% Co/2.0% Re/0.1% Mn/$Al_2O_3$ | 832 | 0.89 |
| 13 | 20% Co/2.0% Re/0.3% Mn/$Al_2O_3$ | 1000 | 0.9 |
| 14 | 20% Co/2.0% Re/1% Mn/$Al_2O_3$ | 920 | 0.89 |
| 15 | 20% Co/1.0% Re/0.25% V/$Al_2O_3$ | 963 | 0.88 |
| 16 | 20% Co/1.0% Re/0.5% V/$Al_2O_3$ | 923 | 0.9 |

General Procedure for Continuous Tests

The catalyst testing unit was composed of a syngas feed system, a tubular reactor, which had a set of wax and cold traps, back pressure regulators, and three gas chromatographs (one on-line and two off-line).

The carbon monoxide was purified before being fed to the reactor over a 22% lead oxide on alumina catalyst placed in a trap to remove any iron carbonyls present. The individual gases or mixtures of the gases were mixed in a 300 mL vessel filled with glass beads before entering the supply manifold feeding the reactor.

The reactor was made of ⅜ in. (0.95 cm) O.D. by ¼ in. (0.63 cm) I.D. stainless steel tubing. The length of the reactor tubing was 14 in. (35.6 cm). The actual length of the catalyst bed was 10 in. (25.4 cm) with 2 in. (5.1 cm) of 25/30 mesh (0.71/0.59 mm) glass beads and glass wool at the inlet and outlet of the reactor.

The wax and cold traps were made of 75 mL pressure cylinders. The wax traps were set at 140° C. while the cold traps were set at 0° C. The reactor had two wax traps in parallel followed by two cold traps in parallel. At any given time products from the reactor flowed through one wax and one cold trap in series. Following a material balance period, the hot and cold traps used were switched to the other set in parallel, if needed. The wax traps collected a heavy hydrocarbon product distribution (usually between $C_6$ and above) while the cold traps collected a lighter hydrocarbon product distribution (usually between $C_3$ and $C_{20}$). Water, a major product of the Fischer-Tropsch process was collected in both the traps.

General Analytical Procedure

The uncondensed gaseous products from the reactors were analyzed using a common on-line HP Refinery Gas Analyzer. The Refinery Gas Analyzer was equipped with two thermal conductivity detectors and measured the concentrations of CO, $H_2$, $N_2$, $CO_2$, $CH_4$, $C_2$ to $C_5$ alkenes/alkanes/isomers and water in the uncondensed reactor products. The products from each of the hot and cold traps were separated into an aqueous and an organic phase. The organic phase from the hot trap was usually solid at room temperature. A portion of this solid product was dissolved in carbon disulfide before analysis. The organic phase from the cold trap was usually liquid at room temperature and was analyzed as obtained. The aqueous phase from the two traps was combined and analyzed for alcohols and other oxygenates. Two off-line gas chromatographs equipped with flame ionization detectors were used for the analysis of the organic and aqueous phases collected from the wax and cold traps.

Catalyst Testing Procedure

Catalyst (3 g) to be tested was mixed with 4 grams of 25/30 mesh (0.71/0.59 mm) and 4 grams of 2 mm glass beads. The 14 in. (35.6 cm) tubular reactor was first loaded with 25/30 mesh (0.71/0.59 mm) glass beads so as to occupy 2 in. (5.1 cm) length of the reactor. The catalyst/glass bead mixture was then loaded and occupied 10 in. (25.4 cm) of the reactor length. The remaining 2 in. (5.1 cm) of reactor length was once again filled with 25/30 mesh (0.71/0.59 mm) glass beads. Both ends of the reactor were plugged with glass wool.

Catalyst activation was subsequently carried out using the following procedure. The reactor was heated to 120° C. under nitrogen flow (100 cc/min and 40 psig (377 kPa)) at a rate of 1.5° C./min. The reactor was maintained at 120° C. under these conditions for two hours for drying of the catalyst. At the end of the drying period, the flow was switched from nitrogen to hydrogen. The reactor was heated under hydrogen flow (100 cc/min and 40 psig (377 kPa)) at a rate of 1.4° C./min. to 350° C. The reactor was maintained at 350° C. under these conditions for sixteen hours for catalyst reduction. At the end of the reduction period, the flow was switched back to nitrogen and the reactor cooled to reaction temperature (usually 220° C.).

The reactor was pressurized to the desired reaction pressure and cooled to the desired reaction temperature. Syngas, with a 2:1 $H_2$/CO ratio was then fed to the reactor when reaction conditions were reached.

The first material balance period started at about four hours after the start of the reaction. A material balance period lasted for between 16 to 24 hours. During the material balance period, data was collected for feed syngas and exit uncondensed gas flow rates and compositions, weights and compositions of aqueous and organic phases collected in the wax and cold traps, and reaction conditions such as temperature and pressure. The information collected was then analyzed to get a total as well as individual carbon, hydrogen and oxygen material balances. From this information, CO Conversion (%), Selectivity/Alpha plot for all ($C_1$ to $C_{40}$) of the hydrocarbon products, $C_5^+$ Productivity (g/hr/kg cat), weight percent $CH_4$ in hydrocarbon products (%) and other desired reactor outputs were calculated.

The results obtained from the continuous-flow Fischer-Tropsch catalyst testing unit is Tables 2 and 3.

Table 2 lists the catalyst composition, CO Conversion (%), Alpha value from the Anderson-Schultz-Flory plot of the hydrocarbon product distribution, $C_5$+ Productivity (g $C_5$+/hour/kgcatalyst) and weight percent methane in the total hydrocarbon product (%).

The temperature was 220° C., the pressure was between 340 psig (2445 kPa) to 362 (2597 kPa) and the space velocity was 2 NL/hour/g. cat. for all the examples in Table 2.

TABLE 2

| Example No. | Catalyst | % Conv. | alpha | $C_5$+ | % $C_1$ |
|---|---|---|---|---|---|
| 17 | 20% Co/1.0% Re/0.01% B/$Al_2O_3$(F) | 86 | 0.85 | 224 | 17.2 |
| 18 | 20% Co/1.0% Re/0.05% B/$Al_2O_3$(F) | 65 | 0.88 | 158 | 18 |
| 19 | 20% Co/1.0% Re/0.1% B/$Al_2O_3$(F) | 92 | 0.88 | 289 | 8.4 |
| 20 | 20% Co/1.0% Re/0.01% P/$Al_2O_3$ | 95 | 0.88 | 276 | 14.1 |
| 21 | 20% Co/1.0% Re/0.05% P/$Al_2O_3$ | 93 | 0.9 | 261 | 13.9 |
| 22 | 20% Co/1.0% Re/0.1% P/$Al_2O_3$ | 87 | 0.9 | 276 | 11.0 |
| 23 | 20% Co/1.0% Re/0.5% P/$Al_2O_3$ | 83 | 0.9 | 170 | 18 |
| 24 | 20% Co/1.0% Re/1% P/$Al_2O_3$ | 93 | 0.91 | 291 | 10.6 |
| 25 | 20% Co/1.0% Re/0.1% B/$Al_2O_3$ | 90 | 0.9 | 269 | 10.2 |
| 26 | 20% Co/1.0% Re/0.5% B/$Al_2O_3$ | 99 | 0.9 | 281 | 13.6 |
| 27 | 20% Co/1.0% Re/0.1% Mn/$Al_2O_3$ | 97 | 0.9 | 263 | 9.6 |
| 28 | 20% Co/2.0% Re/0.3% Mn/$Al_2O_3$ | 92 | 0.91 | 365 | 10.9 |
| 29 | 20% Co/2.0% Re/1% Mn/$Al_2O_3$ | 100 | 0.9 | 272 | 16.6 |

Table 3 lists the catalyst composition, CO Conversion (%), Alpha value from the Anderson-Shultz-Flory plot of the hydrocarbon product distribution, $C_5$+ Productivity (g $C_5$+/hour/kgcatalyst) and weight percent methane in the total hydrocarbon product (%) for examples illustrating the extended lifetimes of the catalysts of the present invention. Example 30 is a comparative example showing results for a supported cobalt/rhenium catalyst without the promoters of the present invention.

Examples 31–34 show the superior results obtained using the catalysts of the present invention after approximately 160 hours of continuous operation. The temperature was 220° C., the pressure was between 340 psig (2445 kPa) to 362 (2597 kPa) and the space velocity was 2 NL/hour/g. cat. for all the examples in Table 3, i.e., the same conditions as for examples 17–29, except for the length of operation.

TABLE 3

| Example No. | Catalyst | % Conv. | alpha | $C_5$+ | % $C_1$ |
|---|---|---|---|---|---|
| 30 | 20% Co/1% Re/$Al_2O_3$ | 77 | 0.88 | 217 | 12 |
| 31 | 20% Co/1% Re/0.5% B/$Al_2O_3$ | 98 | 0.91 | 277 | 13 |
| 32 | 20% Co/1% Re/0.1% B/$Al_2O_3$ | 87 | 0.90 | 267 | 11 |
| 33 | 20% Co/2% Re/0.1% Mn/$Al_2O_3$ | 97 | 0.90 | 263 | 10 |
| 34 | 20% Co/1% Re/1% Mn/$Al_2O_3$ | 100 | 0.91 | 272 | 16 |

While a preferred embodiment of the present invention has been shown and described, it will be understood that variations can be made to the preferred embodiment without departing from the scope of, and which are equivalent to, the present invention. For example, the structure. and composition of the catalyst can be modified and the process steps can be varied.

The complete disclosures of all patents, patent documents, and publications cited herein are incorporated by reference in their entirety. U.S. patent application Ser. No. 09/314,921, entitled Fischer-Tropsch Processes and Catalysts Using Fluorided Supports, filed May 19, 1999, and U.S. patent application Ser. No. 09/314,920, entitled Fischer-Tropsch Processes and Catalysts Using Fluorided Alumina Supports filed May 19, 1999, are incorporated by reference in their entirety.

The foregoing detailed description and examples have been given for clarity of understanding only. No unnecessary limitations are to be understood therefrom. The invention is not limited to the exact details shown and described, for variations obvious to one skilled in the art will be included within the invention by the claims.

We claim:

1. A process for producing hydrocarbons, comprising contacting a feed stream comprising hydrogen and carbon monoxide with a catalyst in a reaction zone maintained at conversion-promoting conditions effective to produce an effluent stream comprising $C_5$ and higher hydrocarbons; said catalyst comprising:

cobalt;

rhenium;

a promoter selected from the group consisting of boron and phosphorous, wherein the promoter is effective to enhance the selectivity of the catalyst for producing the $C_5$ and higher hydrocarbons, wherein the weight ratio of elemental promoter to elemental cobalt is between about 0.0005:1 and 0.5:1; and an alumina support.

2. The process of claim 1 wherein the promoter comprises boron.

3. The process of claim 1 wherein the promoter comprises phosphorous.

4. A process for producing hydrocarbons, comprising contacting a feed stream comprising hydrogen and carbon monoxide with a catalyst in a reaction zone maintained at conversion-promoting conditions effective to produce an effluent stream comprising $C_5$ and higher hydrocarbons, said catalyst comprising:

cobalt;

a promoter comprising phosphorus, wherein the weight ratio of elemental promoter to elemental cobalt is between about 0.00005:1 and 0.5:1; and a support selected from the group consisting of silica, titania, zirconia, alumina, and combinations thereof.

5. The process of claim 4 wherein the catalyst further comprises rhenium.

6. The process of claim 4 wherein the support comprises alumina.

7. The process of claim 4 wherein the support comprises silica.

8. The process of claim 4 wherein the support comprises titania.

9. The process of claim 4 wherein the support comprises zirconia.

* * * * *